United States Patent [19]

Adair

[11] Patent Number: 5,125,395
[45] Date of Patent: Jun. 30, 1992

[54] DEFLECTABLE SHEATH FOR OPTICAL CATHETER

[76] Inventor: Edwin L. Adair, 99 Inverness Dr. East, Englewood, Colo. 80112

[21] Appl. No.: 581,592

[22] Filed: Sep. 12, 1990

[51] Int. Cl.$^5$ .................................................. A61B 1/06
[52] U.S. Cl. .......................................... 128/4; 128/772; 604/95
[58] Field of Search ............... 128/4, 657, 772; 604/95, 170

[56] References Cited

U.S. PATENT DOCUMENTS

| | | |
|---|---|---|
| 2,975,785 | 3/1961 | Sheldon .................. 128/6 |
| 3,266,059 | 8/1966 | Stelle . |
| 3,521,620 | 7/1970 | Cook .................. 128/772 |
| 3,572,325 | 3/1971 | Bazell et al. .................. 128/6 |
| 3,610,231 | 10/1971 | Takahashi .................. 128/6 |
| 3,791,151 | 3/1974 | Fukaumi et al. .................. 128/6 |
| 4,445,892 | 5/1984 | Hussein et al. .................. 128/4 |
| 4,456,017 | 6/1984 | Miles .................. 604/95 |
| 4,499,895 | 2/1985 | Takayama .................. 128/6 |
| 4,646,722 | 3/1987 | Silverstein et al. .................. 128/4 |
| 4,742,817 | 5/1988 | Kawashima et al. .................. 128/4 |
| 4,757,827 | 7/1988 | Buchbinder et al. .................. 604/170 |
| 4,802,461 | 2/1989 | Cho . |
| 4,928,669 | 5/1990 | Sullivan .................. 128/4 |
| 4,934,340 | 6/1990 | Ebling et al. . |

FOREIGN PATENT DOCUMENTS

| | | |
|---|---|---|
| 247371 | 12/1987 | European Pat. Off. . |
| 2926339 | 1/1980 | Fed. Rep. of Germany . |
| 1208639 | 10/1970 | United Kingdom . |
| 1304231 | 1/1973 | United Kingdom . |
| 2130885 | 6/1984 | United Kingdom .................. 128/4 |

OTHER PUBLICATIONS

Kolb "Elastic Linkage is Heart of Steerable Catheter" *Product Engineering*, vol. 40, No. 18, pp. 19-21, Sep. 8, 1969.

*Primary Examiner*—Stephen C. Pellegrino
*Assistant Examiner*—Ralph A. Lewis
*Attorney, Agent, or Firm*—Fields, Lewis, Pittenger & Rost

[57] ABSTRACT

An apparatus is provided having a steerable and removable sheath for use with an optical catheter wherein the sheath with the catheter therein is to be positioned in a pathway leading to a body cavity of a patient for observation and/or treatment. The apparatus comprises an elongated, bendable, hollow body having a distal end, a proximate end and a plurality of channels extending from the proximate end to the distal end. An optical catheter is extendable through one of the channels in the body having a distal end aligned with the distal end of the body and a proximate end extending outwardly beyond the proximate end of the body. The catheter conforms to the shape and movement of the body. A deflectable means is provided adjacent the distal end of the second of the channels to deflect the distal end of the body in a desired direction. A substantially rigid wire is extendable through the second channel to straighten the body during insertion of the sheath in the passageway of the patient and for manipulating the deflectable means after insertion to deflect the body in a desired direction for examination and/or treatment.

2 Claims, 1 Drawing Sheet

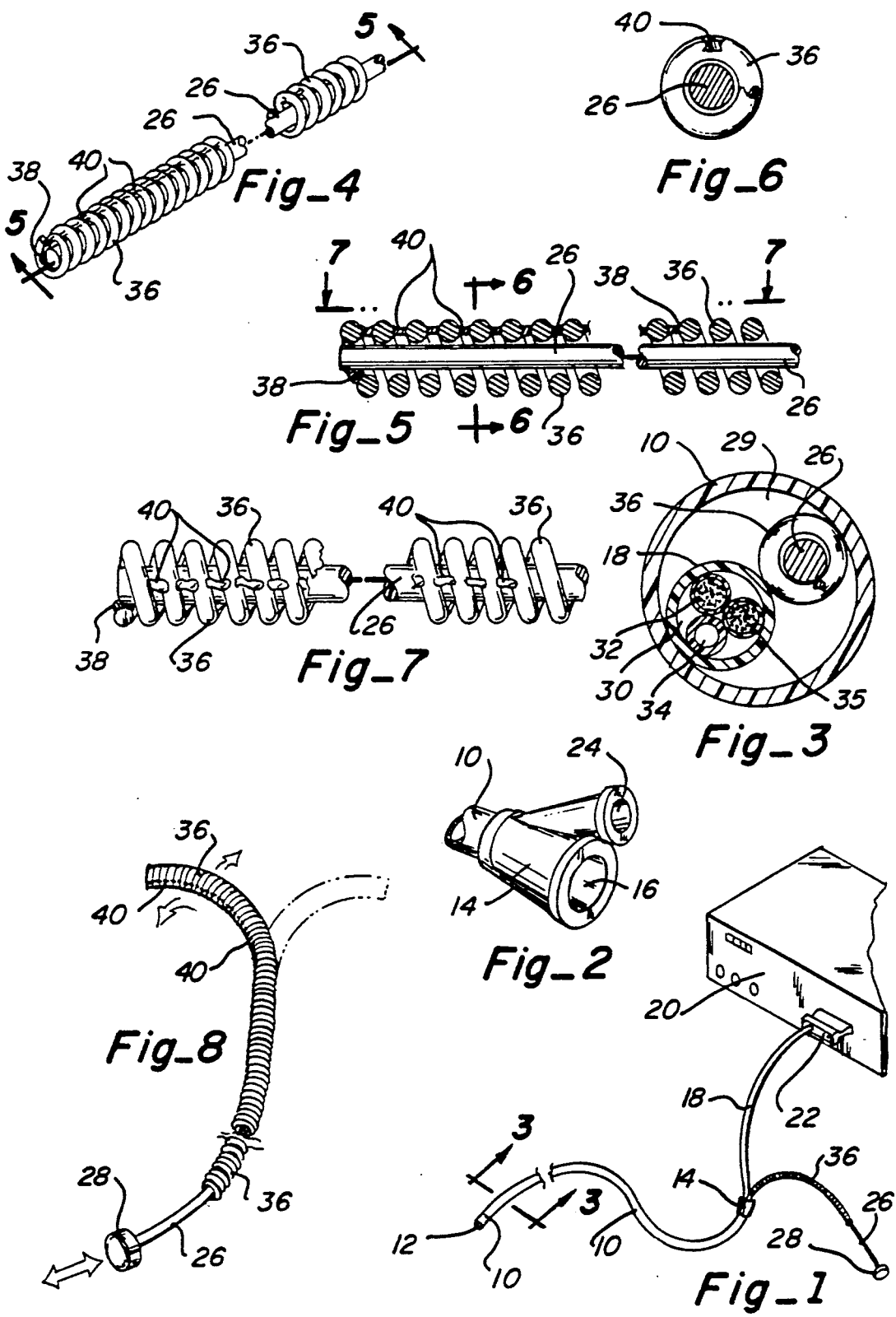

DEFLECTABLE SHEATH FOR OPTICAL CATHETER

TECHNICAL FIELD

The present invention relates to a deformable and removable sheath and more particularly to a deformable and removable sheath for use with an optical catheter. The sheath is constructed so that by pushing or pulling a rod within the sheath the distal end can be bent in a desired direction.

BACKGROUND ART

Most fiber optic endoscopes on the market today are made in a conventional manner wherein they include an elongated body or shaft containing both image fibers and light carrying fibers. The endoscope may also have additional passageways for irrigation and/or for conducting operative or investigative procedures. Sometimes it also will be provided with a steering mechanism for pointing the distal end thereof. Most optical endoscopes are configured in a shape to do one specific examination. For example, one may be a flexible cystourethroscope for examination of the lower genitourinary tract. Another may be a bronchoscope for looking into the respiratory tract. Still another may be a flexible hysteroscope for looking into the uterus. Once any of these devices is manufactured, it is locked into that configuration and generally can only be used for the purpose for which it was constructed. In other words, it is not adaptable for other types of examinations. An exception to this is that in rare instances one may use a flexible hysteroscope for looking into the bladder. If this is done only because the regular scope is broken or unavailable, or done by mistake. There also is a device now available for looking the nasal sinuses This is a small flexible scope which has an eyepiece, a steering mechanism for changing direction of the device to allow its manipulation into a sinus opening and a light connector. However, it cannot be used for any other purpose.

Because of the necessity for providing a variety of types and styles of endoscopes, the cost invested in endoscopes can be quite high, inasmuch as they are not interchangeable.

U.S. Pat. No. 2,975,785 to Sheldon discloses an endoscope with spaced segments interconnected by two pairs of cables located on opposite sides of the segments. Each pair of cables has distal ends which extend around pulleys mounted on a common shaft which is attached to a handle for rotating the shaft. The rotation of the shaft will cause one of the pairs of cables to be shortened and the other to be lengthened so as to bend the distal end of the endoscope in the desired direction. With the two pairs of cables and control means, the endoscope can be bent in any desired direction.

U.S. Pat. No. 3,266,059 to Stelle discloses a prestressed, articulated joint having pivotal segments which are moved by cables. Associated springs prestress the joint.

U.S. Pat. No. 3,572,325 to Bazell et al., discloses an endoscope with spaced annular segments having control cables extending from the distal end to the proximate end where the cables are connected to a wobble plate which is pivoted to lengthen and shorten the cables to create appropriate bending of the endoscope.

U.S. Pat. No. 3,610,231 to Takahashi discloses an endoscope with a stiff central stay and cables which connect to rotatable elements at the proximate end of the endoscope to alternately lengthen and shorten the cables to deflect the distal end of the endoscope in any direction desired. Again, two pairs of cables are provided which are lengthened and shortened together as an appropriate control mechanism is manipulated.

U.S. Pat. No. 3,799,151 to Fukaumi et al., discloses an endoscope with sections that are pivoted together in series and have wires which can be lengthened and shortened for manipulation of the endoscope to cause bending in any desired direction.

U.S. Pat. No. 4,499,895 to Takayama discloses an endoscope with wires that are lengthened and shortened by means of a motor which rotates in response to movement of a control lever.

Although each of these devices is suitable for its intended purpose, each such device is quite complicated in construction and therefore costly. Also, they are of substantial diameter limiting their use and comfort for the patient.

DISCLOSURE OF THE INVENTION

An apparatus is provided having a steerable and removable sheath for use with an optical catheter wherein the sheath with the catheter therein is to be positioned in a pathway leading to a body cavity of a patient for observation and/or treatment. The apparatus comprises an elongated, bendable, hollow body having a distal end, a proximate end and a plurality of channels extending from the proximate end to the distal end. An optical catheter is extendable through one of the channels in the body having a distal end aligned with the distal end of the body and a proximate end extending outwardly beyond the proximate end of the body. The catheter conforms to the shape and movement of the body. A deflectable means is provided adjacent the distal end of the second of the channels to deflect the distal end of the body in a desired direction. A substantially rigid wire is extendable through the second channel to straighten the body during insertion of the sheath in the passageway of the patient and for manipulating the deflectable means after insertion to deflect the body in a desired direction for examination and/or treatment.

The deflectable means can include a spiral spring positioned within the sheath body adjacent the distal end thereof and having a gap between each spiral. This spring has a distal end at the center of the spring and located at the distal end of the sheath body. Means is provided between each spiral along one side thereof to maintain the spacing. The central wire has a distal end fixedly attached to the distal end of the spring so that longitudinal movement of the central wire in a first direction with respect to the spring will deflect the distal end of the spring and the sheath in one direction and movement of the central wire in a second, opposite direction will deflect the distal end of the spring and the sheath body in the opposite direction. The space maintaining means can include a line of solder along one side of the spring which penetrates between each pair of spirals to maintain normal spacing therebetween.

With this invention, it can be seen that a deformable sheath is provided wherein a central wire performs a dual function of straightening the sheath during insertion and providing a means for deflecting the sheath after it is inserted. Because of the simple construction of the device, it can be made at a sufficiently low cost to be disposable after each use to minimize the transfer of disease or infection from one patient to the next. Of course, the catheter can be withdrawn from the first channel before disposing of the sheath so that the more expensive catheter can be reused with a new inexpensive sheath.

Additional advantages of this invention will become apparent from the description which follows, taken in conjunction with the accompanying drawings.

BRIEF DESCRIPTION OF THE DRAWINGS

FIG. 1 is a perspective view showing a deflectable and removable sheath with a central wire deflection mechanism constructed in accordance with the present invention, for use with an optical catheter attached to a console;

FIG. 2 is an enlarged perspective view of the proximate end of the deflectable and removable sheath;

FIG. 3 is a an enlarged vertical section, taken along line 3—3 of FIG. 1, showing details of the inner construction of the removable sheath;

FIG. 4 is a fragmentary perspective view of the distal end of the guide wire of this invention with the deformable and removable sheath removed for clarity of illustration;

FIG. 5 is a horizontal section, taken along line 5—5 of FIG. 4, showing the attachment between the center guide wire and the coil spring and the spacing means between the coil spring;

FIG. 6 is a vertical section, taken along line 6—6 of FIG. 5, showing further details of the invention;

FIG. 7 is a fragmentary top plan view, taken along line 7—7 of FIG. 6, showing still additional details; and FIG. 8 is a perspective view showing the deflection of the coil spring caused by back and forth movement of the guide wire.

BEST MODE FOR CARRYING OUT THE INVENTION

In accordance with this invention, a flexible sheath 10 is provided, as shown in FIG. 1. The sheath 10 has a distal end 12 and a connector 14 at the proximate end. As best seen in FIG. 2, the connector has a central opening 16 for receiving a catheter 18. Conveniently, the proximate end of the catheter 18 is connected to a console 20 by means of an adaptor 22. Connector 14 also has a side opening 24 for receiving a flexible wire 26 having a handle 28 attached to the proximate end thereof for a purpose to be described.

As best seen in FIG. 3, catheter 18 is received in a channel 29 within sheath body 10. Conveniently, channel 30 within catheter 18 can also receive devices, such as a laser fiber 32 for lithotripsy. Similarly, an irrigation passageway 34 can be provided. A fiber optic bundle 35 is also provide which may include one or more optic fibers for transmitting light from console 20 to the distal end of catheter 18 to illuminate the site under investigation. In addition, bundle 35 contains coherent fibers to project an image to a video screen (not shown) associated with console 20. When inserted, these elements will extend through channel 30 to the distal end 12 of sheath 10. Conveniently, connector 14 has a luer lock fitting which mates with a similar fitting on catheter 18 to maintain alignment of the catheter and sheath so that the projected image will be of a known orientation on the video screen.

The guide wire 26 is surrounded by a spirally wound wire or spring 36. The distal ends of the center wire 26 and spring 36 being connected together as by weld 38, shown in FIGS. 4, 5 and 7. A line of solder 40 which extends parallel to center wire 26 is run along one side of spring 36 from the distal end thereof for a substantial distance toward the proximate end. The solder 40 creates a fixed spacing between the spring coils along the side of the solder line. Thus, when the central wire 26 is pushed distally with one hand by handle 28 with respect to the spring 36, while grasping the proximate end of spring 36 with the other hand, the spring will curve in the direction of the solder line, as best seen in FIG. 8. This causes the surrounding sheath 10, which has been omitted from FIGS. 4-8 for clarity of illustration, to be bent in the same direction. When central wire 26 is pulled in the proximate direction by handle 28, the spring 36 will be bent in the opposite direction as shown in dotted lines in FIG. 8. By this means, the end of the sheath can be moved through an arc of approximately 180°. By rotating the sheath within the passageway, observation can be made in any direction through the full 360°.

This invention has been described in detail with reference to a particular embodiment thereof, but it will be understood that various other modifications can be effected within the spirit and scope of this invention.

I claim:

1. An apparatus having a steerable and removable sheath for use with an optical catheter wherein said sheath with the catheter therein is to be positioned in a passageway leading to a body cavity of a patient for observation and/or treatment, said apparatus comprising:

an elongated, bendable, hollow body forming said sheath and having a distal end, a proximate end and a central channel extending from said proximate end to said distal end;

an optical catheter extendable through said channel in said sheath body, having a distal end aligned with said distal end of said sheath body and a proximate end extending outwardly beyond said proximate end of said sheath body, said catheter conforming to the shape and movement of said sheath body;

a spiral spring positioned within said channel of said sheath body adjacent said distal end thereof, said spring having a central distal end at said distal end of said sheath body and having a gap between each spiral thereof;

means between and interconnecting each of said spirals along one side thereof adjacent said distal end to maintain said spacing; and a substantially rigid wire extendable through the center of said spiral spring, having a distal end fixedly attached to said distal end of said spring so that longitudinal movement of said wire in a first direction with respect to said spring will deflect said distal end of said spring and said sheath body in one direction and movement of said wire in a second, opposite direction will deflect said distal end of said spring and said sheath body in the opposite direction.

2. An apparatus, as claimed in claim 1, wherein said space maintaining means includes:

a line of solder along said one side of said spring which penetrates between each pair of spirals to maintain normal spacing therebetween.

* * * * *